United States Patent
Ilan et al.

(10) Patent No.: US 8,962,033 B2
(45) Date of Patent: Feb. 24, 2015

(54) METHOD FOR IMPROVED FIBRIN SEALING

(75) Inventors: Erez Ilan, Kibbutz Netzer Sereni (IL);
Kfir Regev, Tel-Aviv (IL); Israel Nur,
Moshav Timmorim (IL)

(73) Assignee: Omrix Biopharmaceuticals Ltd.,
Rehovot (IL)

( * ) Notice: Subject to any disclaimer, the term of this patent is extended or adjusted under 35 U.S.C. 154(b) by 379 days.

(21) Appl. No.: 13/015,999

(22) Filed: Jan. 28, 2011

(65) Prior Publication Data
US 2011/0182991 A1 Jul. 28, 2011

(51) Int. Cl.
*A61K 9/50* (2006.01)
*A61L 24/10* (2006.01)

(52) U.S. Cl.
CPC .................. *A61L 24/106* (2013.01)
USPC ....................................... 424/499

(58) Field of Classification Search
USPC ........................................ 424/499
See application file for complete search history.

(56) References Cited

U.S. PATENT DOCUMENTS

| | | | |
|---|---|---|---|
| 1,776,489 A | 9/1930 | Cobb | |
| 4,427,650 A | 1/1984 | Stroetmann | |
| 4,631,055 A | 12/1986 | Redl et al. | |
| 4,846,405 A | 7/1989 | Zimmermann | |
| 5,116,315 A | 5/1992 | Capozzi et al. | |
| 5,143,838 A | 9/1992 | Kraus et al. | |
| 5,330,974 A * | 7/1994 | Pines et al. | 514/13.6 |
| 5,582,596 A | 12/1996 | Fukunaga et al. | |
| 5,665,067 A | 9/1997 | Linder et al. | |
| 5,690,675 A | 11/1997 | Sawyer et al. | |
| 5,792,835 A | 8/1998 | Tse et al. | |
| 5,883,078 A | 3/1999 | Seelich et al. | |
| 5,962,405 A | 10/1999 | Seelich | |
| 5,989,215 A | 11/1999 | Delmotte et al. | |
| 6,121,232 A | 9/2000 | Nur et al. | |
| 6,461,361 B1 | 10/2002 | Epstein | |
| 6,585,696 B2 | 7/2003 | Petersen et al. | |
| 6,620,125 B1 | 9/2003 | Redl | |
| 6,802,822 B1 | 10/2004 | Dodge | |
| 7,125,569 B2 | 10/2006 | Nur et al. | |
| 7,196,054 B1 | 3/2007 | Drohan et al. | |
| 7,455,248 B2 | 11/2008 | Kablik et al. | |
| 2010/0203033 A1 | 8/2010 | Nur et al. | |

FOREIGN PATENT DOCUMENTS

| | | |
|---|---|---|
| CN | 1088117 | 6/1994 |
| EP | 1390485 | 10/2006 |
| WO | WO 93/05822 | 4/1993 |
| WO | WO 96/39212 | 12/1996 |
| WO | WO 98/33533 | 8/1998 |
| WO | WO 02/095019 | 11/2002 |
| WO | WO 2007/059801 | 5/2007 |

(Continued)

OTHER PUBLICATIONS

Efthimiou, E. et al. "Fibrin sealant associated with increased body temperature and leukocytosis after laparoscopic gastric bypass" Surgery for Obesity Related Diseases (2009) pp. 1-4.

(Continued)

*Primary Examiner* — Benjamin Packard

(57) ABSTRACT

The present invention relates to a fibrin matrix, its preparation and use for effectively sealing a defect in a mucosa or other moist tissue.

21 Claims, 2 Drawing Sheets

(56) References Cited

FOREIGN PATENT DOCUMENTS

WO   WO 2008/053475   5/2008
WO   WO 2010/095128   8/2010

OTHER PUBLICATIONS

Fullum, T.M. et al. "Decreasing anastomotic and staple line leaks after laparoscopic Roux-en-Y gastric bypass" Surg Endoscop. (2009) vol. 23. pp. 1403-1408.

Hidas, G. et al. "Sutureless nephron-sparing surgery: use of albumin glutaraldehyde tissue adhesive (BioGlue)" Urology (2006) vol. 67, Issue 4 pp. 697-700.

Kamel R.M. "Prevention of postoperative peritoneal adhesions". Eur J Obstet Gynecol Reprod Biol. (2010) 150(2) pp. 111-118.

Kawamura, M. et al. 'The sealing effect of fibrin glue against alveolar air leakage evaluated up to 48h; comparison between different methods of application' European Journal of Cardio-thoracic Surgery 28 (2005) pp. 39-42.

Lillemoe, K.D. et al. 'Does Fibrin Glue Sealant Decrease the Rate of Pancreatic Fistula After Pancreaticoduodenectomy? Results of a Prospective Randomized Trial' (2004) Journal of Surgery, vol. 8, No. 7 pp. 766-774.

Nicoson ZR, Buckley CA. "Bond strength of fibrin glue between layers of porcine small intestine submucosa (SIS)" Biomed Sci Instrum (2002) vol. 38 pp. 179-184.

Vilela, M.L et al. What Is Important for Continent Catheterizable Stomas: Angulations or Extension? Int Braz J Urol. (2007) vol. 33(2) pp. 254-263.

Yo, L.S.F. 'Buttressing of the Staple Line in Gastrointestinal Anastomoses: Overview of New Technology Designed to Reduce Perioperative Complications' Dig Surg (2006) vol. 23 pp. 283-291.

Anonymous, 'Tisseel [Fibrin Sealant] Valupak 10ml' Baxter US Dec. 31, 2001, pp. 1 XP002646839. Retrieved from the Internet: URL:http://www.ecomm.baxter.com/ecatalog/browsecatalog. do?lid=10001&hid=10001&cid=10016 &key=6a263ebfc86bb2656c5fb4cec53e89bc&pid=463470 [retrieved on Jun. 30, 2011].

Anonymous, 'Tisseel [Fibrin Sealant]—Highlights of Prescribing Information' Baxter US Nov. 30, 2009 pp. 1-3 XP002646848. Retrieved from the Internet: URL:http://www.baxter.com/downloads/healthcare_professionals/products/Tisseel_PI.pdf [retrieved on Jul. 1, 2011].

International Search Report re: PCT/IL2011/000092 dated Aug. 5, 2011.

\* cited by examiner

METHOD FOR IMPROVED FIBRIN SEALING

FIELD OF THE INVENTION

The invention relates to a fibrin matrix with improved sealing properties, its preparation and use.

BACKGROUND OF THE INVENTION

Fibrin sealant is typically a blood product obtained from either commercial sources or some regional blood transfusion centers. Components that are commonly used in the preparation of fibrin sealants are predominantly fibrinogen supplemented with various quantities of Factor VIII, Factor XIII, fibronectin, vitronectin and von Willebrand factor (vWF). The fibrinogen component is typically activated by the last protease of the coagulation cascade-thrombin.

Fibrin sealant is formed by an enzymatic reaction involving inter alia, fibrinogen, thrombin and Factor XIII. The thrombin converts the fibrinogen to fibrin by enzymatic action at a rate determined by the concentration of thrombin. Factor XIII, is typically present in the fibrinogen component of the sealant and is an enzyme of the blood coagulation system that cross-links and stabilizes the fibrin clot. This process bypasses most of the steps of normal coagulation and mimics its last phase. Some manufacturers add anti-proteolytic agents to the fibrin sealant formulation (as described in WO 93/05822) or specifically remove the plasminogen in order to stop or delay the fibrinolysis (as described in U.S. Pat. No. 5,792,835 and U.S. Pat. No. 7,125,569).

U.S. Pat. No. 4,427,650 discloses a tissue adhesive which can be applied in the form of dry, powdery mixture immediately and directly onto the wound or in the area of operation. The adhesive consists of solid, powdery, biologically active constituents and contains 60 to 96% by weight of fibrinogen, which is largely liberated from cryo-insoluble globulin, 0.05 to 5% by weight of fibrinolysis inhibitor, and 0.1 to 15% by weight of thrombin and/or prothrombin.

U.S. Pat. No. 5,962,405 discloses a lyophilized fibrinogen preparation for preparing a fibrinogen solution for use as a tissue adhesive. The fibrinogen preparation contains a solubility improving substance.

It has been known for some time that fibrin sealant may be applied to wounds, such as open wounds of a person, to close the wound, stop the bleeding, and prevent other substances, such as infectious agents, from entering the wound.

The effect of fibrin sealant in sealing defects in tissues which are under constant movement, e.g. gastrointestinal tissue and lung tissue, has been reported. However, there is discrepancy in these reports.

One reported approach to diminish post-operative defects such as leaks at the staple or suture (staple/suture) line after gastrointestinal resection is to use staple/suture line reinforcements. Different staple/suture line reinforcement products are commercially available. For example, physicians have tried non- or semi absorbable staple line reinforcement products such as Seamguard®, Peristrips Dry®, and Surgisis®. However, in early experimental and clinical studies, absorbable staple line reinforcement material appears to have considerable advantages over non- or semi absorbable staple line reinforcement material (Yo et al. "Buttressing of the staple line in gastrointestinal anastomoses: overview of new technology designed to reduce perioperative complications". Dig Surg. 2006; 23:283-291). Recent reports using fibrin as absorbable staple line reinforcement for the prevention of gastrointestinal post-operation leaks (Fullum et al. "Decreasing anastomotic and staple line leaks after laparoscopic Roux-en-Y gastric bypass". Surg Endosc. 2009; 23:1403-1408; Efthimiou et al. "Fibrin sealant associated with increased body temperature and leukocytosis after laparoscopic gastric bypass". Surg Obes Relat Dis. 2009 Mar. 17) suggest that the current fibrin sealant formulations are not adequate for staple/suture line reinforcement.

U.S. Pat. No. 5,690,675 discloses closing wounds in lung tissue by a two step method consisting essentially of applying fasteners (e.g. staples, clips, pins, hooks) to a region adjacent to the wound, wherein the fasteners may cause penetrations. The fasteners are present in a preformed layer of collagen, fibrin, fibrinogen, elastin, albumin, or a combination thereof, and energy is applied to the region to fuse the material to the tissue and seal perforations in the tissue.

U.S. Pat. No. 5,883,078 discloses a stable tissue adhesive which comprises fibrinogen and an activator or pro-activator of prothrombin. The adhesive can be present as a liquid or dry preparation. In one embodiment, a solid, 2-sided adhering tissue adhesive is made by applying the dry adhesive in solid form to a wound surface and the second wound surface (the second tissue part) is subsequently adapted and shortly pressed together. The preparation promptly dissolves by means of the blood and/or wound secretion present and subsequently solidifies with the commencement of coagulation, whereby the adhering and hemostatic effect is achieved. The solid, 2-sided adhering tissue adhesive is especially suitable for joining soft tissue parts such as liver or spleen.

Lillemoe et al. [(2004) J Gastrointest Surg., Vol. 8, No. 7 pp 766-774 A journal article entitled "Does Fibrin Glue Sealant Decrease the Rate of Pancreatic Fistula After Pancreaticoduodenectomy? Results of a Prospective Randomized Trial] showed that topical application of fibrin glue sealant to the surface of the pancreatic anastomosis did not reduce the incidence of pancreatic fistula or total complications in patients after pancreaticodudodenectomy and concludes that there seems to be no benefit regarding the use of this substance in this setting.

Another study ("The sealing effect of fibrin glue against alveolar air leakage evaluated up to 48 h; comparison between different methods of application" Kawamura et al. (2005) Eur J of Cardiothorac Surg. 28(1):39-42) discloses the sealing effect of fibrin glue against alveolar air leakage in an animal model and evaluates different methods of application. Solution A consisting of a protein concentrate comprising fibrinogen and a solution B comprising thrombin were used. In the rubbing and spray method, solution A was dripped and gently rubbed onto the air leakage area. Then both solutions were sprayed simultaneously as a mixed aerosol. In another method, a double layer was prepared by dripping solution A onto the air leakage surface after which solution B was dripped. In another method, a collagen fleece coated with dry fibrinogen and thrombin on one side (TachoComb) was used in animal (dog) models and checked after 24 hours. According to the authors, the sealing effect of fibrin glue is relatively unstable up to 12 hours after its application. Also, the authors concluded that the rubbing and spray method may help the fibrin seal to reach its full strength faster compared with the other two methods.

Another study by Yo et al (2006) (Dig Surg 23: 283-291) discloses efforts to reduce anastomotic complications like bleeding or leakage at the staple line when performing gastrointestinal resections. Yo indicated that in animal models of rat colonic anastomosis, the application of fibrin glue to seal and prevent leakage appears not to be a feasible technique. It is disclosed that in gastric resection, the application of fibrin glue to support and seal off the staple line seemed more successful.

U.S. Pat. No. 7,196,054 discloses a method for treating wounded tissue in a patient, comprising applying to the wounded tissue a composition in the form of a dry powder comprising fibrinogen in an amount which forms a fibrin matrix in the presence of thrombin, Factor XIII, $Ca^{2+}$, and aqueous solution; providing to the composition, thrombin, Factor XIII, $Ca^{2+}$ and aqueous solution in amounts which form a fibrin matrix in the presence of fibrinogen.

Fullum et al. (2009) discloses that anastomotic and staple line leaks (ASL) occur after laparoscopic Roux-en-Y gastric bypass (LRYGB) in obese patients. Fibrin sealant was placed along the gastric staple line. The authors concluded that the operative technique, including the proper staple size, staple line reinforcement, handsewn otomy closure, stay sutures, intraoperative leak testing, and fibrin sealants, was instrumental in decreasing the incidence of ASL after LRYGB. The authors were unable to determine if any one component was most crucial in preventing ASL.

In contrast, Efthimiou et al. 2009 discloses that fibrin sealant use had no effect on the anastomotic or staple line leak rate in LRYGB.

There is an unmet need for a superior fibrin sealant formulation for sealing defects in tissues that are in constant movement e.g. gastrointestinal tissue and lung tissue.

SUMMARY OF THE INVENTION

The major current use of fibrin sealants is for hemostasis; this action can be enhanced by autologous coagulation factors, e.g. fibrinogen, present in the blood covering the wounded area.

Another use of the fibrin sealant is sealing tissue leaks such as leaks of air and/or liquids e.g. urine fluids, bowel fluids, seroma. Typically, in these tissue leaks autologous coagulation factors are absent. Most sealants, including synthetic sealants, are not efficient in sealing tissues leaks. Without being bound by the mechanism, the air/liquid may act as a barrier between the sealant and the tissue and thus preventing an intimate contact between the sealant and the tissue.

Generally, surgeons often dry the wounded leaking tissue as much as possible prior to application of the sealant. Often, the drying is carried out manually using a sponge/gauze and a gas spray (Hidas et al. "Sutureless nephron-sparing surgery: use of albumin glutaraldehyde tissue adhesive (BioGlue)". Urology, 2006; 67:697-700). These drying procedures increase the risk of developing tissue adhesion (Kamel R M. "Prevention of postoperative peritoneal adhesions". Eur J Obstet Gynecol Reprod Biol. 2010; 150(2):111-118).

In addition, these drying procedures are also problematic in regions which are non accessible to the surgeon e.g. when performing a laparoscopic process.

The present invention provides a fibrin matrix which is efficient in sealing tissues leaks.

In one aspect, the invention provides a method for applying fibrin matrix onto a moist tissue comprising: applying an effective amount of a solid fibrin sealant blend onto the moist tissue; and applying over at least a portion of the applied solid fibrin sealant blend an effective amount of a liquid fibrin sealant formulation, wherein the effective amounts for solid fibrin sealant blend and liquid fibrin sealant formulation are sufficient to produce a fibrin matrix on the moist tissue having improved sealing strength relative to application of an effective amount of either the liquid fibrin sealant formulation or the solid fibrin sealant blend.

In one embodiment of the present invention, the sealing strength is at least 1.2-fold improved relative to application of the liquid fibrin sealant formulation.

In another embodiment of the present invention, the sealing strength is about 1.7-fold improved relative to application of the liquid fibrin sealant formulation.

In another further embodiment of the present invention, the application is on a tissue which is not enriched, has small amount, is deprived or lacks blood vessels and/or tissues which are oozing or non-bleeding.

In one embodiment of the present invention, the solid fibrin sealant blend comprises a solid component comprising fibrinogen and a solid component comprising a proteolytic enzyme component which is capable of forming fibrin when it reacts with fibrinogen.

In another further embodiment of the invention, fibrinogen comprising component of the solid fibrin sealant blend is prepared by a step of drying a fibrinogen-containing solution having a fibrinogen concentration of less than 25 mg/ml.

In one embodiment of the invention, the fibrinogen concentration is about 20 mg/ml.

Yet in another embodiment of the invention, the proteolytic enzyme is thrombin.

Yet in another further embodiment of the invention, the application is on a tissue defect.

Still in another embodiment of the invention, the application is on at least a part of a staple or suture line present in the tissue.

Another aspect of the invention relates to a method for preparing a fibrin matrix on a wet surface comprising the steps of: providing a solid component comprising fibrinogen; providing a solid component comprising a proteolytic enzyme which is capable of forming fibrin when it reacts with fibrinogen; providing a liquid fibrin sealant formulation; applying an effective amount of the solid components onto at least a part of the wet surface; and applying over at least a portion of the applied solid components an effective amount of the liquid fibrin sealant formulation.

In one embodiment of the invention, the wet surface is fibrinogen free.

In another embodiment of the invention, the liquid fibrin sealant formulation is provided in solid form and reconstituted prior to its application.

In another further embodiment of the invention, the liquid fibrin sealant formulation is provided in frozen form and thawed prior to its application.

Still in another embodiment of the invention, the solid component is provided in liquid form and dried prior to its application.

Yet in another embodiment of the invention, the solid component is provided in frozen form and dried prior to its application.

Yet in another further embodiment of the invention, the solid components are applied simultaneously or one after the other.

In another embodiment of the present invention, the liquid components are applied simultaneously or one after the other.

In another further embodiment of the present invention, the solid components are provided in a blend.

In one embodiment of the present invention, the surface is a tissue.

In one embodiment of the present invention, the tissue is not enriched, has small amount, is deprived or lacks blood vessels and/or is oozing or non-bleeding.

In another aspect the invention relates to a fibrin matrix obtainable according to the invention.

Yet in another aspect the invention provides a method for treating or preventing a defect in a moist tissue of a subject in need comprising the steps of:

a) providing a component comprising solid fibrinogen, providing a component comprising a solid proteolytic enzyme which is capable of forming fibrin when it reacts with fibrinogen; and providing a liquid fibrin sealant formulation;

b) applying an effective amount of the solid components of a) onto at least a part of the moist tissue; and c) applying over at least a portion of the applied solid components an effective amount of the liquid fibrin sealant formulation of a).

In one embodiment of the present invention, the moist tissue is not enriched, has small amount, is deprived or lacks blood vessels and/or is oozing or non-bleeding.

In another embodiment of the present invention, the defect is a leak in the tissue.

In another further embodiment of the present invention, the leaking substance is not enriched, has small amount, is deprived or lacks plasma or blood components.

In one embodiment of the present invention, the liquid fibrin sealant formulation is provided in solid form and reconstituted prior to its application.

In another further embodiment of the invention, the liquid fibrin sealant formulation is provided in frozen form and thawed prior to its application.

In one embodiment of the invention, the solid component is provided in liquid form and dried prior to its application.

Yet in another embodiment of the invention, the solid component is provided in frozen form and dried prior to its application.

Yet in another further embodiment of the invention, the solid components are applied simultaneously or one after the other.

In one embodiment of the invention, the liquid components are applied simultaneously or one after the other.

In another embodiment of the invention, the solid components of a) are provided in a blend.

In another further embodiment of the invention, the defect is a staple or a suture.

In one aspect, the invention provides a kit comprising: (i) container(s) comprising solid components comprising (a)—fibrinogen component and (b)—a proteolytic enzyme component which is capable of forming fibrin when it reacts with fibrinogen, wherein the (a) and (b) components are in separate containers or in the same container as a blend; and (ii) at least two separated containers, the at least one separated container comprises a liquid, frozen or solid fibrinogen component, and the at least second separated container comprises a liquid, frozen or solid proteolytic enzyme component which is capable of forming fibrin when it reacts with fibrinogen, wherein when the at least two separated containers of (ii) comprise solid components, then the (a) and (b) components are in the same container as a blend.

In one embodiment of the present invention, the proteolytic enzyme is thrombin.

In another embodiment of the present invention, the kit is used for applying onto a wet surface.

In another further embodiment of the present invention, the kit is used for sealing leaks in tissues which are not enriched, have small amount, are deprived or lack blood vessels and/or tissues which are oozing or non-bleeding.

The fibrin matrix or the kit according to the invention can be used for treating or preventing a defect in a moist tissue.

DETAILED DESCRIPTION OF EMBODIMENTS OF THE INVENTION

Figure 1:
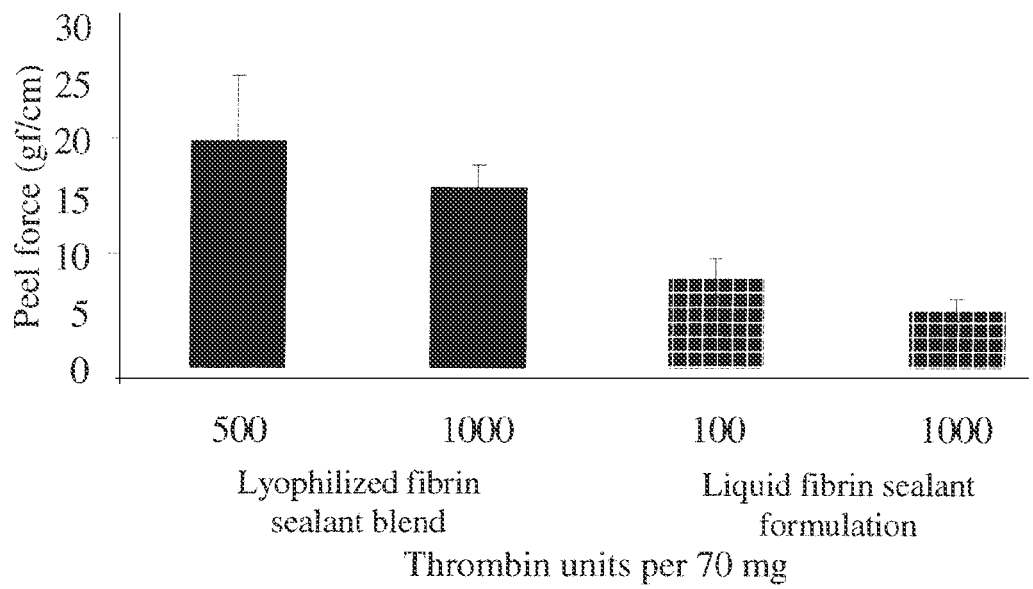
FIG. 1 shows the force needed to separate two layers of ileum intestine tissue (peel force) which were bonded together using two different fibrin sealant formulations: a mixture of lyophilized fibrinogen and thrombin versus a two component liquid fibrin sealant formulation.

The invention relates to a method for applying fibrin matrix onto a mucosa or other moist tissue, the method comprises the sequential application of a solid fibrin sealant blend onto the surface of the tissue followed by application of a liquid fibrin sealant formulation over of at least a portion of the surface. The invention also relates to the effective sealing of a defect in a mucosa or other moist tissue by the sequential application of first a solid fibrin sealant blend followed by a liquid fibrin sealant formulation.

The invention is based on the following findings:

The adhesive force (or peel force) of the different tested fibrin formulations was tested by the peel test. The test measures the bond strength of fibrin glue between layers of porcine small intestine submucosa. In one embodiment, the tested adhesive formulation was applied onto the serosal side of a pig's ileum. Following application of the tested fibrin sealant formulation the ileum tissue was folded upon itself (serosa to serosa) and the fibrin sealant formulation was allowed to polymerize. The force needed to separate the two adhered ileum tissue layers from one another (peel force) was measured using a Universal Tensile Testing Machines—Lloyd Instruments LFPLUS. Typically, the higher the measured peel force, the greater the adhesive force of the tested formulation. It was found according to the present invention that the adhesive force is significantly improved when using a lyophilized fibrin sealant formulation as compared to using a liquid fibrin sealant formulation. It was found that the adhesive force of the lyophilized fibrin sealant formulation was about 2.7-fold higher as compared to the adhesive force of the liquid fibrin sealant formulation.

The sealing properties of different fibrin formulations were measured by the burst test. The burst test can determine and evaluate the ability of a sealant to prevent leakage. Briefly, an aluminum pipe that is connected to a water source and contains holes is introduced into a tubular segment of pig ileum and the tubular segment is sealed and tightened on both ends of the pipe. Upon allowing water flow into the aluminum pipe, water enters into the void between the ileum and the aluminum pipe through the holes in a way that backflow of water into the aluminum pipe is prevented. Before allowing the water flow, a 10 mm incision is formed perpendicular to the intestine length and the incision is first sutured in its midline and then the tested fibrin sealant formulation is applied onto the incision area through a 6 cm$^2$ parafilm template frame that is placed around the incision area. After application of the tested formulation, the fibrin is left to cure (or polymerize) for 10 minutes and the intestine is filled with water to test its ability to withstand pressure. Once the water flows into the void between the ileum and the pipe the water pressure increases until the sealing of the incision opens and a sharp drop in the pressure is observed. The pressure level is monitored using a pressure gauge (D-logmate 590 MRC Israel) that is connected to the liquid flow line. The observed pressure before the drop is recorded and considered as the burst pressure. Typically, a higher observed burst pressure indicates greater sealing property of the tested formulation.

It was also found according to the invention that the lyophilized fibrin sealant, which had been shown to have better adhesive forces than the liquid fibrin sealant, was not effective in sealing. In contrast, the liquid fibrin sealant formulation had a better sealing effect than the lyophilized fibrin sealant.

It was also surprisingly found that a sequential application of a lyophilized fibrin sealant and a liquid fibrin sealant formulation showed a synergistic increase in the sealing property. About 1.7-fold increase in the sealing strength was observed as compared to the sealing strength of the liquid fibrin sealant formulation. However, a synergistic increase in the sealing properties was not found using the sequential application of lyophilized fibrinogen or lyophilized thrombin followed by administration of a liquid fibrin sealant formulation.

Also, it was found that drying the mucous prior to application of the liquid fibrin sealant formulation (e.g. by applying a protein powder such as albumin powder onto the mucous layer) did not increase the sealing performance of the liquid fibrin sealant formulation.

These findings encouraged development of an improved method of producing a fibrin matrix with greater sealing strength on a mucosa or other moist tissue. The fibrin matrix generated according to the invention can be used for sealing defects in mucosa or other moist tissue e.g. in tissues that are in constant movement e.g. gastrointestinal tissue and lung tissue.

The term "tissue" refers to an association of cells and/or cell components united in carrying out a particular function. The cells in the tissue may be all of one type or of more than one type. The tissue can be an artificial tissue in which cells are grown to function in a similar manner as a tissue in a living organism. The tissue may be a human body tissue or an animal tissue.

The term "fibrin matrix" refers to the fibrin obtained by the sequential application of the solid fibrin sealant blend and the liquid fibrin sealant formulation.

The term "effective amount of a solid fibrin sealant blend" refers to an amount of a solid component comprising fibrinogen and an amount of a solid component comprising a proteolytic enzyme which is capable of forming fibrin when it reacts with fibrinogen which after hydration on a moist tissue forms a fibrin clot.

The term "effective amount of a liquid fibrin sealant formulation" refers to an amount of a liquid component comprising fibrinogen and an amount of a liquid component comprising a proteolytic enzyme (which is capable of forming fibrin when it reacts with fibrinogen) which allow fibrin clot formation after mixing of the liquid components.

Without being bound by the mechanism, it appears that once the solid sealant blend is applied onto the moist tissue it is hydrated. The hydrated solid sealant blend primes the tissue by solidifying the liquid present in the moist tissue and forming a fibrin layer in close proximity to the tissue. The liquid fibrin sealant formulation is then applied on this primed tissue consequently resulting in improved seal strength and durability.

Advantageously, solidifying the moist on the surface without the need of a sponge or gauze may decrease the risk of postoperative adhesion formation.

The term "adhesion" refers to an abnormal attachment between tissues and/or organs. Typically, adhesions occur after surgical procedures such as following rough manipulation of tissues; following tissue surface drying; and/or due to the presence of reactive foreign bodies (e.g. suture materials, talc powder or lint residues) in the operated area.

The term "mucosa" or "mucosa tissue" refers to a moist tissue that covers some organs and body cavities. Typically, the mucosa tissue secretes the mucous material. Examples of mucosa tissue include, but are not limited to, oral mucosa e.g. buccal and sublingual; nasal mucosa; eye mucosa; genital mucosa; rectal mucosa; aural mucosa; lung mucosa; bronchial mucosa; gastric mucosa; intestinal mucosa; olfactory mucosa; uterine mucosa; and esophageal mucosa. The term "mucous" refers to a wet/moist and viscous material such as a substance rich in mucins, glycoprotein's albumin, and/or any other component contributing to viscosity.

The term "other moist tissue" refers to a wet tissue. The tissue can be wet from body fluids such as serum, serum infiltrate, blood and inflammation fluids and/or from other fluids/liquids such as phosphate buffered saline (PBS). In one embodiment of the invention, the fluid does not contain clotting factors (e.g. does not contain fibrinogen).

As used herein, the term "defect" refers to a tear, aperture, bore, fissure, puncture, hole, crack, opening, slit, gap, perforation, fracture, puncture or rupture, leak e.g. in a tissue. E.g. the defect can be formed following an anastomosis procedure. The defect can be congenital e.g. hernia; a condition resulting from body related pathology e.g. seroma, hernia, infection, inflammation; formed after surgery, suturing and/or stapling; or a condition resulting from a non body factor e.g. accidents, injuries.

The term "leak" refers to the escape or pass of a substance e.g. fluid, viscous material and/or air e.g. through a tear, aperture, bore, fissure, puncture, hole, crack, opening, slit, gap, perforation, fracture, puncture or rupture in a tissue.

The term "anastomosis" typically refers to a surgical procedure which is used to reconnect two or more sections of an organ or tissue. The procedure can be used following sectioning of the urinary tract (urethra), throat (esophagus), or in bowel surgery. The procedure can also be used following the excision of a diseased tissue (such as inflamed, cancerous or otherwise pathological tissue e.g. ulcerative disease).

The invention also relates to a kit comprising: (i) container (s) comprising solid components comprising (a)—fibrinogen component and (b)—a proteolytic enzyme component which is capable of forming fibrin when it reacts with fibrinogen; and (ii) at least two separated containers, the at least one separated container comprises a liquid, frozen or solid fibrinogen component, and the at least second separated container comprises a liquid, frozen or solid proteolytic enzyme component which is capable of forming fibrin when it reacts with fibrinogen.

The (a) and (b) components of element (i) can be in separated containers or in the same container as a blend. In one embodiment, when the at least two separated containers of (ii) comprise solid components, then the (a) and (b) components are in the same container as a blend. In another embodiment, when the at least two separated containers of (ii) comprise solid components, at least one container comprising an aqueous solution for their hydration is included.

In contrast to commercial fibrin kits which are intended especially for hemostasis, the kit of the invention is also suitable for sealing leaks in tissues which are not enriched, have small amounts, are deprived or lack blood vessels.

Non limiting examples of tissues which are not enriched, have small amounts or are deprived or lack blood vessels are dura, bladder, eyes, lungs and gall bladder.

In one embodiment of the invention, the kit is for sealing leaks in tissues which are not enriched, have small amounts or are deprived or lack blood vessels.

The term "hemostasis" refers to the ability of an agent to stop the bleeding from an injured blood vessel and/or to contribute to keeping the blood contained within the blood vessel.

Also, in contrast to commercial fibrin kits which are intended especially for stopping the bleeding from an injured blood vessel and/or for keeping the blood contained within the blood vessel, the kit of the invention is also suitable for sealing leaks of non blood or plasma substances, e.g. cerebrospinal fluid (CSF), air, intestinal content, bile, lymph fluid and vitreous humor.

In one embodiment, the fibrin matrix or the kit of the invention is for sealing leaks in tissues which are oozing or non-bleeding. The term oozing refers for example to minor bleeding. The term oozing includes cases of bleeding where a relatively low volume of blood is lost at a relatively low rate.

The kit can also contain instructions for use. The kit may also comprise means for cutting and/or stapling or suturing a tissue or an organ such as mechanical or manual cutting and stapling devices. The container can be a vial, a pre-filled syringe, a small bottle, a tube or any other suitable container which contains the solid or the liquid components. The container can be of different sizes and contain different volumes/weights of the compositions, for example, each liquid component can have a volume of equal to or less than about 10 ml, and each solid component can have a powder weight of equal to or less than about 3 g. Optionally, an applicator for the administration of the solid and the liquid components can also be included in the kit.

The fibrin matrix or kit according to the invention can be used in any therapeutic purpose. The term "any therapeutic purpose" refers to any curative or preventive treatment in a subject. Exemplary of therapeutic purposes include, but are not limited to, sealing a bore hole formed in a tissue or organ e.g. a bone; anastomosis at blood vessels; joining tissue parts e.g. soft tissue parts; treating or preventing dura defects e.g. tears and leaks following dural injections, fissures or cracks; treating or preventing bleeding; treating or preventing air leaks such as following pulmonary lung resection; treating or preventing defects following intestinal perforation; treating or preventing defects following anastomosis procedure carried out in any tissue e.g. uterine, esophagus, stomach, pancreas, pancreatic duct, gall bladder, bile duct, intestinal (including the small intestine and the large intestine), and rectum; treating or preventing post-operation leaks in any tissue e.g. uterine, esophagus, stomach, pancreas, pancreatic duct, gall bladder, bile duct, intestinal (including the small intestine and the large intestine), and rectum; preventing or diminishing the occurrence of post-operative leaks at the staple or suture line e.g. by applying the fibrin matrix according to the invention onto at least a part of a defect such as a staple/suture line; for strongly affixing prosthesis e.g. during a hernia operation; for staple/suture line reinforcement; to prevent or diminish alveolar air leakage; treating or preventing renal defects; treating or preventing fistulas; treating or preventing heart defects e.g. penetrating heart wounds; reinforcing of a vascular graft prosthesis; and treating or preventing cerebrospinal fluid leakage.

In one embodiment of the invention, the therapeutic use is for sealing leaks in tissues which are not enriched with blood vessels or lack blood vessels.

In another embodiment of the invention, the therapeutic use is for enforcement of staple/suture line.

The fibrin matrix of the invention can be used for sealing defects without the need of staples or sutures.

The term "staple or suture" includes any fastener which is used for closing a wound such as, but not limited to, staple, clip, pin, hook, suture and the like.

The term "at least a part of a defect", as used herein, refers to an area which is smaller, equal, or larger than the defect. E.g. the area can be 1, 10, 20, 30, 40, 50, 60, 70, 80, 90 or 100%, including any range between the disclosed percentages, of the defect or larger. In one embodiment of the invention, the fibrin matrix or kit according to the invention is used for staple/suture line reinforcement. For example, a 10 mm incision formed in a subject during a surgery operation is first sutured or stapled. For reinforcement 100 mg solid fibrin sealant blend (1000 IU thrombin per 70 mg fibrinogen) is applied onto the staple/suture line followed by spraying of a liquid fibrin sealant formulation. The liquid fibrin is applied by spraying in a total volume of 2 ml (1:1 ratio between the two components) of 1000 IU/ml thrombin and 70 mg/ml fibrinogen.

The term "subject" as used herein includes animals of mammalian origin, including humans. In one embodiment, the subject is a patient.

In one aspect, the invention provides a method for applying fibrin matrix onto moist tissue. The method comprises the following steps: applying an effective amount of a solid fibrin sealant blend onto the moist tissue; and applying over at least a portion of the solid fibrin sealant blend an effective amount of a liquid fibrin sealant formulation, wherein the effective amounts of solid fibrin sealant blend and liquid fibrin sealant formulation are sufficient to produce a fibrin matrix on the moist tissue having improved sealing strength relative to application of an effective amount of either the liquid fibrin sealant formulation or the solid fibrin sealant blend. Advantageously, the application of the solid fibrin sealant before the liquid fibrin sealant improves the sealing strength of the liquid fibrin sealant.

The term "moist tissue" refers to a wet tissue and includes e.g. mucosa, mucosa tissue and other moist tissue. In another embodiment of the invention, the tissue is moist from a fluid which is fibrinogen free. The term "fibrinogen free" refers, for example, to a fibrinogen concentration of lower than 1.5 g/L.

The term "over at least a portion of the solid fibrin sealant blend", as used herein, refers to an area which varies from a smaller surface area to a larger surface area as compared to the area where the solid fibrin sealant component(s) was applied to. For example, the liquid fibrin sealant formulation can be applied to 1, 10, 20, 30, 40, 50, 60, 70, 80, 90 or 100%, including any range between the disclosed percentages, of the surface area where the solid component(s) was applied to. Alternatively, the liquid fibrin sealant formulation can be applied to a larger surface area than the area where the solid component(s) was applied to, e.g. the entire moist tissue or organ.

The term "liquid fibrin sealant formulation" refers, for purposes of this application, to at least two separated liquid components required for the formation of fibrin sealant. The at least one separated component comprises fibrinogen, and the at least second separated component comprises a proteolytic enzyme which is capable of forming fibrin when it reacts with fibrinogen (or a fibrinogen-containing formulation). When the at least two separated components are administered e.g. injected into the target site, the liquid components come into contact, mimicking the final stages of the blood coagulation cascade process, in order to form the well known clot, fibrin.

The term "soft tissue" typically refers to structures of the body that connect, support, envelope and/or surround other structures and organs. The soft tissue can be a connective tissue or a non connective tissue. Examples of soft tissue include, but are not limited to, tendons, ligaments, fibrous tissues, synovial membrane, fascia, muscles, muscle wall, nerves, intestine, fat tissue, liver, skin, spleen and blood vessels.

The term "solid fibrin sealant blend" refers, for purposes of this application, to a solid composition that comprises the precursors for the formation of a fibrin sealant. The composition comprises a solid proteolytic enzyme which is capable of forming fibrin when it reacts with fibrinogen (or a fibrinogen-containing formulation) and solid fibrinogen. The solid bland can also comprise other components such as albumin. The proteolytic enzyme can be thrombin and/or a substance obtainable from snake venom. In one embodiment of the invention, the solid composition comprises a fibrinogen and thrombin components in their lyophilized form. In another embodiment, thrombin and fibrinogen containing solutions are separately dried e.g. by lyophilization to produce their respective solid components in the overall solid fibrin sealant blend. In another embodiment of the invention, the resulting solid materials are ground into powders using a superfine mill or a cooled blade mill or manually by passing the solid material through a sieve e.g. by using a spatula. In one embodiment of the invention, the material was grounded with a spatula through a 200 µm sieve. In another embodiment of the invention, the solid materials are ground into powders using a method as described in WO 2008/053475, which is incorporated herein by reference.

The particle size of the solid material following milling can be lower than 1000 µm. In one embodiment of the invention, the particle size of the solid material following milling is equal to or less than 200 µm. The particle size distribution can be in the range of 10 to 100 µm or in the range of 10 to 60 µm. The solid proteolytic enzyme and the solid fibrinogen can be provided together. It is also possible that the solid precursors are provided separately and applied simultaneously or one after the other onto the desired surface. In one embodiment of the invention, the solid proteolytic enzyme and the solid fibrinogen are supplied as a blend.

The invention also provides a method for preparing a fibrin matrix on a wet surface. The method comprises the steps of: providing a solid component comprising fibrinogen; providing a solid component comprising a proteolytic enzyme which is capable of forming fibrin when it reacts with fibrinogen; providing a liquid fibrin sealant formulation; applying an effective amount of the solid components onto at least a part of the wet surface; applying over at least a portion of the solid components an effective amount of the liquid fibrin sealant formulation.

The term "wet surface" refers to a moist surface. The surface can be a mucosa, mucosa tissue and/or other moist tissue. The surface can be wet from body fluids such as serum infiltrate, blood and inflammation fluids and/or from non bodily fluids such as PBS.

The wet surface can be a surface of a body part of a patient e.g. any tissue that contains liquids or air. The term "surface" includes, but is not limited to, the genital area, including the uterus, vagina and ovaries; the lungs; the anus; the spleen; the liver; the dura mater; the renal; the esophagus; the stomach; the pancreas; the pancreatic duct; the gal bladder; the bile duct; the intestine (including the small intestine and the large intestine); and the cardiac muscle. The surface can be a bleeding or a non-bleeding site. In one embodiment of the invention, the surface is a non-bleeding site. In another embodiment of the invention, the surface is wet from a fluid which is coagulation factor free (e.g. free of fibrinogen). The surface can also be any surface e.g. a working surface, a surface of a prosthetic device.

The term "at least a part of the wet surface", as used herein, refers to an area which is smaller, equal, or larger than the wet surface. E.g. the area can be 1, 10, 20, 30, 40, 50, 60, 70, 80, 90 or 100%, including any range between the disclosed percentages, of the surface or larger.

The term "over at least a portion of the solid component(s)" refers to an area which varies from a smaller surface area to a larger surface area as compared to the area where the solid fibrin sealant component(s) was applied to. For example, the liquid fibrin sealant formulation can be applied to 1, 10, 20, 30, 40, 50, 60, 70, 80, 90 or 100%, including any range between the disclosed percentages, of the surface area where the solid component(s) was applied to. Alternatively, the liquid fibrin sealant formulation can be applied to a larger surface area where the solid component(s) was applied to e.g. the entire surface.

The solid components in the solid fibrin blend react once hydrated e.g. upon contact with the moist tissue to form a fibrin sealant. Typically, fibrinogen preparations have relatively low solubility and mucous tissue exhibit relatively low liquid content. Advantageously, the fibrinogen component of the solid fibrin sealant blend used can be rapidly dissolved and/or hydrated upon application onto the tissue.

It was found according to the present invention that a solid fibrinogen prepared by a step of lyophilizing a fibrinogen-containing solution having a fibrinogen concentration of 20 mg/ml was reconstituted in an aqueous solution at room temperature in a time period of less than 10 minutes. In one embodiment of the invention, the fibrinogen component of the solid fibrin sealant blend is prepared from a fibrinogen-containing solution having a fibrinogen concentration of equal to or less than 150 such as equal to or less than 85, 25 mg/ml or less than 20 mg/ml.

The solid fibrin sealant blend can be prepared by drying a liquid fibrin sealant formulation. Any drying procedure known in the art can be used including, but not limited to, lyophilization (freeze drying) or spray drying procedures. The drying can be carried out at different temperatures using various drying equipments, such as controlled humidity chamber, drying oven, drying tunnel, vacuum drier, or in any other suitable method which does not affect clot formation.

The term "solid", as used throughout this specification, refers to a composition comprising a liquid content of less than 5% such as less than 4, 3, 2, 1% or lower by weight based on the total weight of the dry composition. The term "solid" is interchangeable with the term "dry" or "powder".

The solid fibrin sealant can be applied onto the tissue by a dispenser. Examples of dispensers are shown in U.S. Pat. No. 1,776,489 and U.S. Pat. No. 7,455,248, which are incorporated herein by reference.

The term "improved sealing strength" refers, for example, to a sealing strength which is at least about 1.2-fold higher compared to the sealing strength obtained by liquid sealant alone. In one embodiment of the invention, the sealing strength is about 1.7-fold higher relative to application of the liquid fibrin sealant formulation. The sealing strength can be measured e.g. by the burst test described above.

"1.2-fold higher improved sealing strength" refers to a sealing strength which is 20% higher than the sealing strength achieved by application of a liquid fibrin sealant formulation. "1.7-fold higher improved sealing strength" refers to a sealing strength which is 70% higher than the sealing strength achieved by application of a liquid fibrin sealant formulation.

The proteolytic enzyme can be thrombin and/or a substance obtainable from snake venom. The liquid components can be frozen until use (e.g. at a temperature of −18° C. or lower) or dried e.g. by lyophilization for prolonged storage. The dried components can be reconstituted by the addition of various volumes of pharmaceutically acceptable carrier prior to use. The term a "pharmaceutically acceptable carrier" refers to any diluent or a vehicle which is suitable for human or other animal use. The carrier can be selected from any of the carriers known in the art such as, but not limited to, phosphate buffered solution (PBS), saline, sodium chloride solution, calcium chloride solution, lactated ringers (LR), 5% dextrose in normal saline, and water for injection. Lyophilized fibrinogen can be reconstituted with sterile water before use. Lyophilized thrombin can be reconstituted with sterile calcium chloride solution or water, such as distilled water, before use. Reconstituted lyophilized fibrinogen and thrombin can be used in the liquid fibrin sealant formulation, which can then be combined to form the fibrin. The two components can be applied onto the desired site simultaneously or one after the other.

In one embodiment of the invention, the fibrinogen comprising component is comprised of a biologically active component (BAC) which is a solution of proteins derived from blood plasma. This component can further comprise tranexamic acid and arginine or lysine or mixtures of arginine and lysine, or their pharmaceutically acceptable salts.

BAC can be derived from cryoprecipitate, such as concentrated cryoprecipitate. The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitated supernatant that contains fibrinogen and factor XIII. The precipitate can be collected, for example by centrifugation. Typically, BAC comprises Factor VIII, fibronectin, von Willebrand factor (vWF), vitronectin, etc. for example as described in U.S. Pat. No. 6,121,232 and corresponding published PCT application WO 98/33533, each incorporated herein by reference.

BAC can comprise stabilizers such as arginine hydrochloride. Typically, the amount of fibrinogen in BAC is in the range of from about 40 to about 60 mg/ml. The amount of tranexamic acid in the solution of BAC can be from about 80 to about 110 mg/ml. The amount of arginine hydrochloride can be from about 15 to about 25 mg/ml.

Optionally, the solution is buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml.

In another embodiment, the concentration of plasminogen and plasmin in the BAC composition is lowered to equal or less than 15 µg/ml like for example 5 µg/ml or less plasminogen, e.g. using a method as described in U.S. Pat. No. 7,125,569 and corresponding published PCT application WO 02/095019, each incorporated herein by reference.

It is also possible that the fibrin sealant formulation comprises components which encourage the formation of the clot, such as $Ca^{2+}$, Factor VIII, fibronectin, vitronectin, von Willebrand factor (vWF) which can be provided as a separate component or formulated with the liquid components.

The liquid fibrin sealant formulation may be applied onto the tissue using a dispenser that ejects the sealant directly onto the tissue or other substrate or working surface with or without air spray e.g. by dripping. In one embodiment of the invention, the sealant is sprayed at air pressure of 15 PSI. Examples of tissue sealant dispensers are shown in U.S. Pat. Nos. 4,631,055, 4,846,405, 5,116,315, 5,582,596, 5,665,067, 5,989,215, 6,461,361 and 6,585,696, 6,620,125 and 6,802,822, and PCT Publication No. WO 96/39212, WO 2007/059801, and WO 2010/095128, all of which are incorporated herein by reference.

A liquid fibrin sealant formulation comprises at least two components prior to the application in surgical operations. In one embodiment, the liquid fibrin sealant formulation comprises two liquid components, one component comprises fibrinogen and upon exposure to a second component which comprises a proteolytic enzyme such as human thrombin a fibrin clot is formed. During surgical operations, the separated liquid components e.g. two liquid components are applied, for example, by two syringes which are emptied simultaneously or one after the other resulting in mixing of the two components and formation of fibrin.

In one embodiment of the invention, the proteolytic enzyme is human thrombin having an activity of from about 2 to about 4,000 IU/ml. The clotting activity of thrombin can be measured directly, for example, according to the European Pharmacopoeia Assay (0903/1997) procedure and/or indirectly, such as by measuring migration length on a slanted surface (the "drop test" as described in published US patent application 2010/0203033) or by any other method known in the art. It is understood by the skilled person that a fibrin glue may be defined by its content of clottable protein instead of the definition based on clottable fibrinogen.

In another embodiment of the invention, the fibrinogen and proteolytic enzyme components are applied in such a way that equal volumes of the two components are mixed and applied onto the patient at the site of the respective wound. Of course, it is to be understood that the fibrin matrix of the invention can be employed during surgical operations and also in other situations where bleeding must be stopped.

The solid fibrin sealant blend can be prepared by mixing solid fibrinogen and solid thrombin in any desired range of ratios. For example, when the solid fibrinogen component was prepared from a fibrinogen containing solution having a fibrinogen concentration of 40-85 mg/ml and the solid thrombin component was prepared from a thrombin containing solution having a thrombin concentration of about 800-1200 IU/ml the two solid components can be mixed in a ratio of 1:1, 3.2:1, 6.4:1, respectively, and so on. The mixing can be carried out in a humidity controlled area (relative humidity 25%, temperature of 37° C.). The mixed powder can be kept in a closed chamber until use.

The fibrinogen containing solution can be diluted e.g. to contain 25 mg/ml or 20 mg/ml fibrinogen prior to the drying step. The mixing of the two components can be carried out prior to application of the solid fibrin sealant blend onto the tissue or applied in the desired ratio immediately onto the tissue.

During application of the liquid fibrin sealant formulation onto the tissue, the fibrinogen containing component and the thrombin containing component may be applied in any desired range of ratios. For example, when the concentration of the fibrinogen component is 40-85 mg/ml and the thrombin concentration is about 800-1200 IU/ml the two components can be mixed in a ratio of 1:1, 1:2, 1:3, 1:4, 1:5, 1:6, respectively, and so on. In one embodiment of the invention, the components of the liquid fibrin sealant are applied in a ratio of 1:1.

The fibrin matrix of the invention can be applied in a therapeutically effective amount. The term "a therapeutically effective amount" refers to the dose required to prevent or treat a disease, disorder or condition. The effective dose can be changed depending on the age and weight of the subject, the disease and its severity (e.g. the incision's size) and other factors which can be recognized by the skilled in the art. For example, the solid fibrin sealant blend can be applied in a weight in the range of 0.1 to 100 mg per cm$^2$ such as in a weight of 0.5, 1, 4, 8, 16, 30, 60 or 100 mg per cm$^2$. The liquid fibrin sealant formulation can be applied in a volume range of from about 0.01 to about 1 ml per cm$^2$ such as in a volume of 0.01, 0.05, 0.5 or 1 ml per cm$^2$.

In one embodiment, for a 10 mm incision, the sequential application is carried out onto a 6 cm$^2$ area by dispersing 100 mg solid fibrin sealant blend (1000 IU thrombin per 70 mg fibrinogen), followed by spraying of a liquid fibrin sealant formulation. The liquid formulation is applied by spraying in a total volume of 2 ml (1:1 ratio between the two components) of 1000 IU/ml thrombin and 70 mg/ml fibrinogen.

The liquid fibrin sealant formulation can be provided in the methods of the invention in solid form and reconstituted prior to its application. Reconstitution can be carried out by the addition of various volumes of a pharmaceutically acceptable carrier. The term "reconstitution" refers to a process in which solid is converted into a liquid form. A reconstituted product can be a liquid product made by adding aqueous liquid to dry solids from which the liquid has been previously removed.

Alternatively, the liquid fibrin sealant formulation can be provided in frozen form, e.g. at a temperature of –18° C. or lower, and thawed prior to its application. The thawing can be carried out by incubating the containers comprising the liquid components at room temperature (20° C. to 25° C.), at a temperature of 2 to 8° C. or at a temperature of 37° C. In another embodiment, the liquid components are applied simultaneously. Yet in another further embodiment, the liquid components are applied one after the other. The solid component can be provided in liquid form and dried prior to its application e.g. by lyophilization (freeze drying) or spray drying procedures. Alternatively, the solid component can be provided in frozen form and dried prior to its application. The frozen components can be thawed and then dried or can be converted directly from frozen into a solid e.g. by sublimation.

The solid component can be provided in suspension e.g. in any suitable solvent including a non-aqueous liquid, such as hydrofluorocarbon (HFE) or any other carrier fluid in which the solid component do not dissolve in, such as alcohols, ethers or other organic fluids. The solid components and/or the liquid components can be applied in the methods of the invention simultaneously or one after the other. In one embodiment, the solid components are provided in a blend and are applied simultaneously. In another embodiment, the solid components are provided in separate containers and are applied simultaneously. In another further embodiment, the solid components are provided in separate containers and are applied one after the other.

The fibrin matrix of the invention can be applied by any means used by surgeons for treatment or prevention of defects including, but not limited to, open surgery, and minimal invasive procedure (MIS), such as in a laparoscopic procedure. In one embodiment of the invention, an incision is made at the site of surgery and the fibrin matrix is applied onto the defect. In another embodiment, an incision is made at the site of surgery, the incision is stapled or sutured and the fibrin matrix is applied onto the staple or suture line. The patient can receive local, regional or general anesthesia. The term "open surgery" refers to surgery wherein the surgeon gains direct access to the surgical site by a relatively large incision.

As used herein the term "minimally invasive procedure" refers to a surgery wherein the surgeon gains access to the surgical site via small incisions or through a body cavity or anatomical opening e.g. via laparoscopy. Specialized techniques can be used to visualize the operated area such as, miniature cameras with microscopes, tiny fiber-optic flashlights and high definition monitors. Instruments having "end effectors" such as forceps, cutters, needle holders, cauterizers, and the like, can be introduced to the surgical site.

Fibrinogen and thrombin containing components are available from manufacturers such as OMRIX e.g. EVICEL®, QUIXIL®, ADHEXIL™; EVITHROM®; Baxter e.g. TISEEL®; CSL e.g. Beriplast® and the like. In one embodiment, the liquid fibrin sealant components are manufactured from pooled human source plasma and provided as a single use kit consisting of two vials: One vial contains a Biological Active Component 2 (BAC2) and another vial contains thrombin. The kit may further include a sterile application device and instructions for use.

In one embodiment, the BAC2 component is a sterile solution at pH 6.7-7.2, which consists mainly of a concentrate of human fibrinogen. Fibrinogen is a protein from human blood that forms a clot when combined with thrombin. Liquid fibrin sealant formulation, such as the BAC2 solution can contain: concentrate of human fibrinogen (55-85 mg/ml), arginine hydrochloride, glycine, sodium chloride, sodium citrate, calcium chloride, and water for injection (WFI).

In one embodiment, the thrombin component is a sterile solution, pH 6.8-7.2, which contains highly purified human thrombin that activates clotting of the final combined product. Thrombin is a highly specific protease that transforms the fibrinogen contained in BAC2 into fibrin. The thrombin solution can contain: human thrombin (800-1200 IU/ml), calcium chloride, human albumin, mannitol, sodium acetate and water for injection.

Cryoprecipitate, which can be the starting material for BAC2, and cryo-poor plasma, which can be the starting material for the production of thrombin can both be made from pooled human source plasma. The steps for the production of cryoprecipitate and cryo-poor plasma are well-known. In one embodiment, thrombin is manufactured by chromatographic purification of prothrombin from cryo-poor plasma followed by activation with calcium chloride e.g. as described in U.S. Pat. No. 5,143,838, which is incorporated herein by reference. In another embodiment, the fibrinogen component is derived from cryoprecipitate, in particular concentrated cryoprecipitate.

The fibrinogen and thrombin components used above as either part of the two liquid fibrin sealant component or the lyophilized component can be prepared from plasma of human beings or mammals. However, it is also possible that the components are prepared by recombinant methods. The fibrinogen components can be prepared in accordance with the processes described in U.S. Pat. No. 6,121,232 and published PCT application WO 98/33533, wherein the plasmin (ogen) is removed, as described in published EP application EP 1,390,485, and tranexamic acid is not added.

Fibrin sealant components, whether as part of the two component liquid fibrin sealant or the solid fibrin sealant blend, derived from blood or blood fractions are typically subjected to at least two discrete virus inactivation/removal steps. Virus inactivation and removal processes can be carried out e.g. by the following methods: nanofiltration; solvent/detergent; low pH treatment, UV irradiation; sodium thiocyanate treatment and/or by any other method known in the art.

The term "virus inactivation step" refers to a situation wherein viruses are maintained in the solution but are rendered non-viable e.g. by dissolving their lipid coat. The term "virus removal step" refers to a situation wherein viruses are physically removed from the solution e.g. by size exclusion techniques.

The term "at least two discrete virus inactivation/removal steps" involves carrying out at least two different and independent treatments for inactivating or removing viruses. A combination of two or more of the following non limiting treatment examples can be used: pasteurization, Solvent/Detergent (S/D), nanofiltration, low pH treatment, UV irradiation and sodium thiocyanate treatment.

The use of a BAC derived from concentrated cryoprecipitate is advantageous since such a fraction contains besides fibrinogen also valuable blood components which play an important role for blood-clotting when a proteolytic enzyme such as human thrombin is contacted with a BAC solution. Valuable components are, for example, factor VIII, factor XIII, fibronectin, vitronectin, von Willebrand factor (vWF), etc.

Application of the solid fibrin sealant blend composition followed by the liquid fibrin sealant composition generates a fibrin matrix on the tissue with a sealing superiority not achieved by application of either of the sealant compositions alone. The fibrin matrix generated according to the invention is especially suitable for sealing defects in mucosa tissues and other enteral or moist tissue that are in constant movement e.g. gastrointestinal tissue. For example, the fibrin of the invention can be used to prevent leak complications occurring in stapled resection or anastomosis in gastrointestinal surgery. In addition, the fibrin of the invention can be advantageously used for strongly affixing prosthesis during a hernia operation.

The disclosures of applications, patents and publications, cited above or below, are hereby incorporated by reference.

The present invention is further described by reference to the following non-limiting examples.

EXAMPLES

Materials and Methods

Lyophilization.
Lyophilization was carried out according to the following cycle:

| Step | Phase | Time (h:m) | Temp (° C.) | Vacuum (mBar) |
| --- | --- | --- | --- | --- |
| 1 | Start values | -:- | 4 | OFF |
| 2 | Freezing | 1:00 | −30 | OFF |
| 3 | Freezing | 1:00 | −50 | OFF |
| 4 | Freezing | 5:40 | −50 | OFF |
| 5 | Preparation | 0:20 | −45 | OFF |
| 6 | Sublimation | 0:15 | −42 | 0.2 |
| 7 | Sublimation | 0:15 | −25 | 0.2 |
| 8 | Sublimation | 25:00 | −25 | 0.2 |
| 9 | Sublimation | 1:00 | −15 | 0.2 |
| 10 | Sublimation | 12:00 | −15 | 0.2 |
| 11 | Sublimation | 2:00 | 20 | 0.2 |
| 12 | Sublimation | 5:00 | 20 | 0.2 |

-continued

| Step | Phase | Time (h:m) | Temp (° C.) | Vacuum (mBar) |
| --- | --- | --- | --- | --- |
| 13 | Second drying | 0:30 | 25 | 0.12 |
| 14 | Second drying | 18:00 | 25 | 0.12 |

Liquid Fibrinogen and Thrombin.

In the experiments below the two liquid components of EVICEL® Fibrin Sealant (BAC2 and Thrombin; Omrix Biopharmaceuticals Ltd.) were used as the two component liquid fibrin sealant. The fibrinogen component (comprising 70 mg of fibrinogen/ml) was used as is and, unless indicated otherwise, the thrombin component was used as is (1000 IU/ml) or diluted 10-fold with a dilution buffer [0.04 M $CaCl_2$ in distilled, deionized water (DDW)]. In all the experiments the liquid fibrin sealant was sprayed at air pressure of 15 PSI.

Preparation of Lyophilized Fibrinogen and Thrombin Mixture.

The compositions of the solutions used to prepare the lyophilized powders were as the two liquid components of EVICEL®. Each of the components was separately lyophilized according to the lyophilzation cycle described above. The fibrinogen component was diluted with DDW to a concentration of 20 mg/ml fibrinogen prior to the lyophilzation procedure.

Following the lyophilization, the powders were milled by a spatula through a 200 μm sieve. The fibrinogen and thrombin milled powders were mixed in a weight ratio of 3.2:1 (equals to a ratio of 1000 IU thrombin per 70 mg fibrinogen as in EVICEL) or 6.4:1 (equals to a ratio of 500 IU thrombin per 70 mg fibrinogen), respectively. The mixing was carried out in a humid control area (relative humidity 25%, temperature of 37° C.). The mixed powder was kept in a closed chamber until use. A fresh powder mixture was prepared for each experiment.

Example 1

The Adhesive Force of Lyophilized Fibrin Sealant and Liquid Fibrin Sealant Formulations In the following experiment, the adhesive forces of lyophilized fibrin sealant and liquid fibrin sealant formulations were measured.

The evaluation was carried out by the peel force test, essentially as described in Nicoson Z R, Buckley C A. "Bond strength of fibrin glue between layers of porcine small intestine submucosa (SIS)". Biomed Sci Instrum. 2002; 38:179-184. Briefly, the tested adhesive formulation was applied onto the serosal side of a pig's ileum (a segment of 4×10 cm) within a 4×4 cm (16 $cm^2$) parafilm template frame (see application manner below).

Following application of the different fibrin sealant formulations, the parafilm template was removed, and the ileum tissue was folded upon itself (serosa to serosa) and left for polymerization for 10 min at room temperature (about 20-25° C.). To obtain four replicates, the segment was cut to strips of 1×10 cm and the force needed to separate the two adhered ileum tissue layers from one another (known as peel force) was measured using a Universal Tensile Testing Machines— Lloyd Instruments LFPLUS.

The tested formulations were applied in the following manner

The liquid fibrinogen and thrombin components were applied by spraying equal volumes of fibrinogen and thrombin and a total volume of 2 ml. Thrombin was applied at two different concentrations, 100 or 1000 IU/ml and fibrinogen at 70 mg/ml; and 400 mg of each lyophilized mixture (a mixture containing 500 or 1000 IU thrombin per 70 mg fibrinogen prepared as specified in the materials and methods section) was applied to within the 16 cm$^2$ parafilm template (100 mg was applied to each replicate). Then, in order to prevent the tissue from drying, PBS was sprayed onto the powder until the powder appeared wet.

The adhesive forces of the different tested formulations are shown in FIG. 1.

It was observed that a higher force was needed in order to peel the two layers of intestine tissue when fibrin was formed by the lyophilized composition compared to the force needed when the liquid fibrin sealant composition was used (compare the peel force of the lyophilized formulation and the liquid formulation when applied at the same concentration of 1000 IU thrombin per 70 mg fibrinogen).

It was therefore found that the adhesive force between two samples is significantly improved when using a lyophilized formulation.

Also, it was observed that a solid fibrinogen prepared by a step of lyophilizing a fibrinogen-containing solution having a fibrinogen concentration of 20 mg/ml was reconstituted in an aqueous solution at room temperature in a time period of less than 10 minutes. The lower fibrinogen concentration yields a more porous lyophilized cake and more porous particles following milling of the cake. It is believed that the increase in porosity enables liquid to more easily enter the particles resulting in a faster re-hydration time.

Example 2

The Sealing Property of Different Fibrin Sealant Formulations

The previous example shows that using a lyophilized formulation increases the adhesive force. In this experiment, the sealing properties of three different fibrin sealant formulations were tested: a mixture of lyophilized fibrinogen and thrombin, a liquid fibrin sealant formulation, and a fibrin sealant formed by the sequential application of a mixture of lyophilized fibrinogen and thrombin followed by an application of a liquid fibrin sealant formulation. The burst test [essentially as described in Vilela et al. "What Is Important For Continent Catheterizable Stomas: Angulations or Extension? Int Braz J Urol. 2007; Vol. 33(2): 254-263] was carried out to determine and evaluate the ability of a sealant to effectively seal and withstand pressure.

The burst pressure in this model indicates on the ability of a tested formulation to adhere to the tissue and maintain its mechanical integrity up to the pressure point in which a burst of the sealing occurs resulting in immediate loss of pressure and visible water leakage.

As described above, a specially designed aluminum pipe (length of 27 cm) containing holes was inserted into a tubular segment of pig ileum in the length of 25-30 cm. The tubular segment was sealed on both ends to the pipe by plastic discs and tightened using metal screws. The aluminum pipe was connected to a water source. Upon allowing water flow into the aluminum pipe, water entered into the void between the ileum and the aluminum pipe through the holes present around the pipe, in a way that backflow of water into the aluminum pipe was prevented.

Before allowing the water flow, a 10 mm incision was formed perpendicular to the intestine length using a sharp blade. To better simulate clinical settings, the incision was first sutured in its midline (using one 3×0 suture; ETHICON; Cat. Number ss684), and then the tested fibrin sealant formulation was applied onto the incision area through a parafilm template frame (20×30 mm; 6 cm$^2$) which was placed around the incision area. After application of the tested formulation (see below the application) the fibrin was left to cure for 10 min, the intestine was filled with water and its ability to withstand pressure was tested. Once the water flows into the void between the ileum and the pipe the water pressure increases until the sealing of the incision opens and a sharp drop in the pressure is observed. The observed pressure level was monitored using a pressure gauge (D-logmate 590 MRC Israel) which was connected to the liquid flow line until a sharp drop in the pressure curve was observed. The pressure before the drop was recorded and considered as the burst pressure.

The tested formulations were applied as follows:

The liquid fibrin was applied by spraying in a total of 2 ml (1:1 ratio between the two components). Only one concentration of thrombin was tested in this experiment: 1000 IU per 70 mg fibrinogen.

100 mg of the lyophilized mixture was dispersed within the 6 cm$^2$ template. Only one mixture was tested: a mixture containing 1000 IU thrombin per 70 mg (a lyophilized fibrinogen and thrombin component mixed in a ratio of 3.2:1 prepared as described in the materials and methods section). In order to prevent the tissue from drying, PBS was sprayed following dispersion of the lyophilized formulation.

The sequential application was carried out by dispersing 100 mg lyophilized fibrinogen and thrombin (1000 IU thrombin per 70 mg), followed by spraying of liquid fibrinogen and thrombin components (2 ml total). If the lyophilized powder was not completely wet by the mucous surrounding the intestine, PBS was sprayed following dispersion of the lyophilized formulation.

Figure 2:
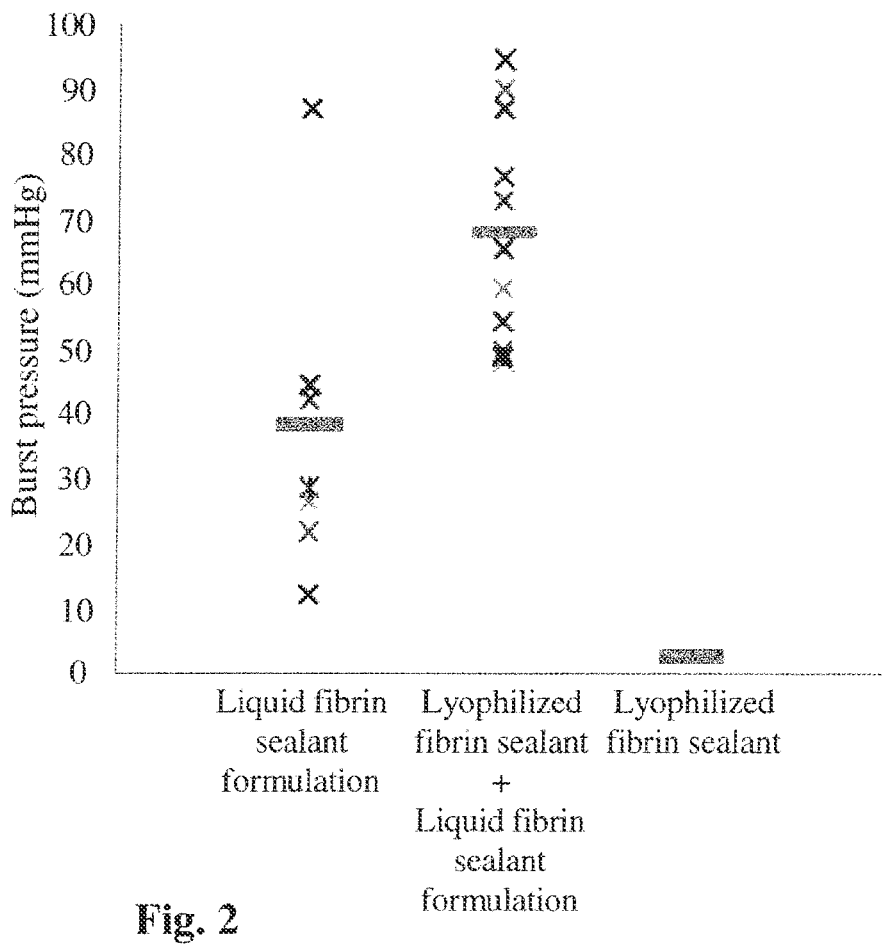
FIG. 2 shows the sealing strength (measured by the burst test) of a mixture of lyophilized fibrinogen and thrombin, a two component liquid fibrin sealant formulation and a fibrin matrix formed by a sequential application of lyophilized fibrinogen and thrombin and a two component liquid fibrin sealant.

It was observed that the lyophilized fibrin sealant, which had better adhesive forces than the liquid fibrin sealant (see FIG. 1), was not effective in sealing (a low burst pressure value was obtained; FIG. 2).

The liquid fibrin sealant showed better sealing effect than the lyophilized fibrin sealant. Surprisingly, the sequential application of lyophilized fibrin sealant prior to liquid fibrin sealant spraying showed an increase greater than merely additive combination in the sealing property. It was therefore found that the sealing property of a sequential application of powder and liquid sealants was superior as compared to the sealing properties of each formulation separately.

Without being bound by the mechanism, it appears that the lyophilized fibrinogen and thrombin powders are dissolved in the mucous surrounding the intestine tissue thus forming a layer of fibrin in close proximity to the serosal tissue. When liquid fibrin sealant is sprayed after the lyophilized powders, a synergistic improvement as described above of tissue sealing is observed (FIG. 2).

Example 3

The Superior Sealing Effect of a Fibrin Formulation Formed by Application of Solid Fibrin Sealant Blend Followed by a Liquid Fibrin Sealant Formulation In the previous examples it was shown that fibrin sealant formed by a sequential application of lyophilized fibrinogen and thrombin mixture followed by liquid fibrin sealant spraying has a superior sealing property.

The following example examines the sealing performance of individual application of only one of the lyophilized components (either fibrinogen or thrombin) followed by application of the liquid fibrin sealant using the burst test method. The following example also examines whether application of albumin to the incision which dries the mucous surrounding the intestine may help the fibrin sealant to better adhere to the tissue and thereby increase the sealing performance of the sealant.

For this purpose the above described burst test (Example 2) was carried out and the sealing property of the following fibrin sealants was evaluated: a fibrin formed by application of 25 mg lyophilized thrombin (prepared from a solution comprising 1000 IU/ml thrombin as the thrombin liquid component of EVICEL; 625 μl solution was lyophilized) followed by spraying of 2 ml liquid fibrin sealant; a fibrin formed by application of 75 mg lyophilized fibrinogen (prepared from a solution comprising 20 mg/ml fibrinogen as described above) followed by spraying of 2 ml liquid fibrin sealant; a fibrin formed by application of 100 mg of a mixture of lyophilized fibrinogen and thrombin (in 3.2:1 weight ratio prepared as described above) followed by spraying of 2 ml liquid fibrin sealant; and a fibrin formulation formed by application of 100 mg albumin powder (Sigma; Cat. num. 078k1503) followed by spraying of 2 ml liquid fibrin sealant. All powders (including the albumin powder) were milled by a spatula through a 200 μm sieve prior to use.

Figure 3:
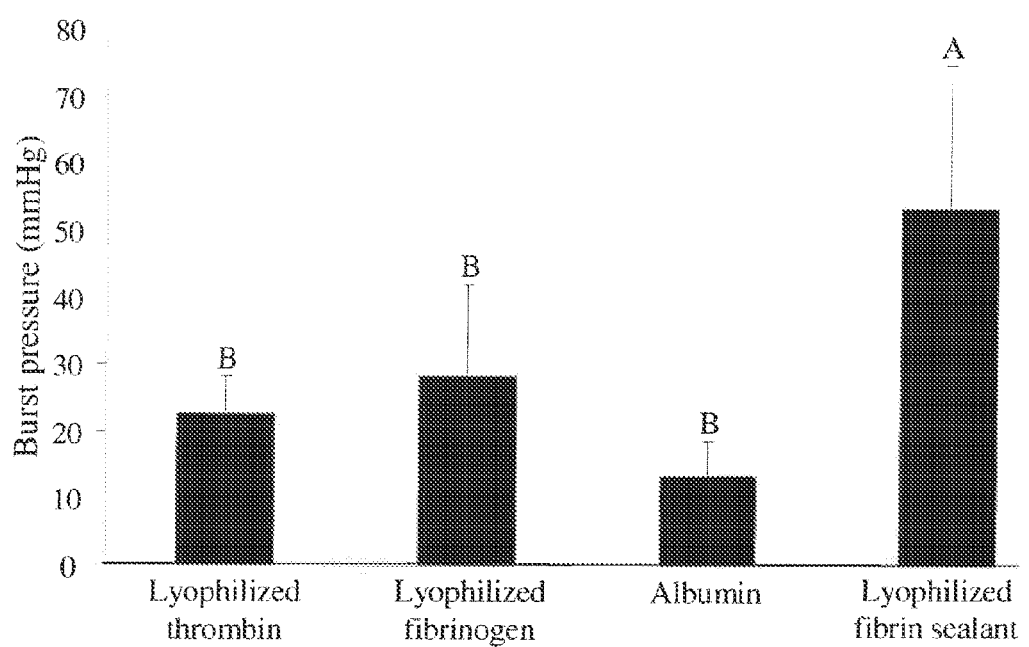
FIG. 3 shows the sealing strength (measured by the burst test) of a fibrin formed by application of lyophilized thrombin followed by spraying of a liquid fibrin sealant; a fibrin formed by application of lyophilized fibrinogen followed by spraying of a liquid fibrin sealant; a fibrin formed by application of a mixture of lyophilized fibrinogen and thrombin followed by spraying of a liquid fibrin sealant; and a fibrin formulation formed by application of albumin powder followed by spraying of a liquid fibrin sealant.

The results are presented in FIG. 3. Statistics was carried out by Tukey-Kramer one way ANOVA test. Same letters represent mean values that are not significantly different ($p>0.05$) and a different letter represent a mean value which is significantly different ($p \leq 0.05$). It was observed that the sequential application of a solid fibrin sealant followed by a liquid fibrin sealant formulation generate a fibrin matrix with a superior sealing property as compared to a fibrin matrix formed by the individual application of only one of the lyophilized components (either fibrinogen or thrombin) followed by application of the liquid formulation. Also, it was found that application of a protein powder (e.g. albumin) which dries the mucous does not increase the sealing performance of the liquid fibrin sealant formulation.

What is claimed is:

1. A method for applying fibrin matrix onto a moist tissue comprising:
   a) applying an effective amount of a solid fibrin sealant blend onto the moist tissue, wherein the solid fibrin sealant blend comprises a solid component comprising fibrinogen and a solid component comprising a proteolytic enzyme component which is capable of forming fibrin when it reacts with fibrinogen; and
   b) applying over at least a portion of the applied solid fibrin sealant blend an effective amount of a liquid fibrin sealant formulation,
wherein the effective amounts for solid fibrin sealant blend and liquid fibrin sealant formulation are sufficient to produce a fibrin matrix on the moist tissue having improved sealing strength relative to application of an effective amount of either the liquid fibrin sealant formulation or the solid fibrin sealant blend.

2. The method according to claim 1, wherein the sealing strength is at least 1.2-fold improved relative to application of the liquid fibrin sealant formulation.

3. The method according to claim 1, wherein the sealing strength is about 1.7-fold improved relative to application of the liquid fibrin sealant formulation.

4. The method according to claim 1, wherein the application is on a tissue selected from the group consisting of: a tissue which is not enriched with blood vessels, a tissue that has a small amount of blood vessels, a tissue that is deprived of blood vessels, a tissue that lacks blood vessels, an oozing tissue and a non-bleeding tissue.

5. The method according to claim 1, wherein the solid fibrin sealant blend comprises a solid component comprising fibrinogen and a solid component comprising a proteolytic enzyme component which is capable of forming fibrin when it reacts with fibrinogen.

6. The method according to claim 1, wherein the fibrinogen comprising component of the solid fibrin sealant blend is prepared by a step of drying a fibrinogen-containing solution having a fibrinogen concentration of less than 25 mg/ml.

7. The method according to claim 6, wherein the fibrinogen concentration is about 20 mg/ml.

8. The method according to claim 1, wherein the proteolytic enzyme is thrombin.

9. The method according to claim 1, wherein the application is on a tissue defect.

10. The method according to claim 1, wherein the application is on at least a part of a staple or suture line present in the tissue.

11. A method for preparing a fibrin matrix on a wet surface comprising the steps of: providing a solid component comprising fibrinogen; providing a solid component comprising a proteolytic enzyme which is capable of forming fibrin when it reacts with fibrinogen; providing a liquid fibrin sealant formulation; applying an effective amount of the solid components onto at least a part of the wet surface; and applying over at least a portion of the applied solid components an effective amount of the liquid fibrin sealant formulation.

12. The method according to claim 11, wherein the wet surface is fibrinogen free.

13. The method according to claim 11, wherein the liquid fibrin sealant formulation is provided in solid form and reconstituted prior to its application.

14. The method according to claim 11, wherein the liquid fibrin sealant formulation is provided in frozen form and thawed prior to its application.

15. The method according to claim 11, wherein the solid component is provided in liquid form and dried prior to its application.

16. The method according to claim 11, wherein the solid component is provided in frozen form and dried prior to its application.

17. The method according to claim 11, wherein the solid components are applied simultaneously or one after the other.

18. The method according to claim 11, wherein the liquid components are applied simultaneously or one after the other.

19. The method according to claim 11, wherein the solid components are provided in a blend.

20. The method according to claim 11, wherein the surface is a tissue.

21. The method according to claim 20, wherein the tissue is selected from the group consisting of: a tissue which is not enriched with blood vessels, a tissue that has small amount of blood vessels, a tissue that is deprived of blood vessels, a tissue that lacks blood vessels, an oozing tissue and a non-bleeding tissue.

* * * * *